US012023458B2

(12) United States Patent
Harada et al.

(10) Patent No.: US 12,023,458 B2
(45) Date of Patent: Jul. 2, 2024

(54) PROGRAMMABLE VALVE FOR THE TREATMENT OF HYDROCEPHALUS

(71) Applicants: HP BIOPRÓTESES LTDA, São Paulo—SP (BR); F&F SAÚDE LTDA., São Paulo—SP (BR)

(72) Inventors: Nikolas Harada, São Paulo (BR); Elias Pereira de Magalhães, São Paulo (BR); Fernando Campos Gomes Pinto, São Paulo (BR)

(73) Assignee: F & F SAÚDE LTDA., São Paulo (BR)

(*) Notice: Subject to any disclaimer, the term of this patent is extended or adjusted under 35 U.S.C. 154(b) by 641 days.

(21) Appl. No.: 17/273,914

(22) PCT Filed: Sep. 6, 2019

(86) PCT No.: PCT/BR2019/050379
§ 371 (c)(1),
(2) Date: Mar. 5, 2021

(87) PCT Pub. No.: WO2020/047642
PCT Pub. Date: Mar. 12, 2020

(65) Prior Publication Data
US 2021/0330947 A1   Oct. 28, 2021

(30) Foreign Application Priority Data
Sep. 6, 2018 (BR) .................. 10 2018 068025 0

(51) Int. Cl.
A61M 27/00 (2006.01)
(52) U.S. Cl.
CPC ... A61M 27/006 (2013.01); A61M 2202/0484 (2013.01); A61M 2205/04 (2013.01); A61M 2205/103 (2013.01)

(58) Field of Classification Search
CPC ........ A61M 27/006; A61M 2202/0484; A61M 2205/04; A61M 2205/103;
(Continued)

(56) References Cited

U.S. PATENT DOCUMENTS

| 4,443,214 A | 4/1984 | Marion | |
| 4,483,366 A * | 11/1984 | Labita | F16K 35/06 70/179 |
| 5,643,194 A * | 7/1997 | Negre | F16K 35/16 604/9 |
| 6,840,917 B2 | 1/2005 | Marion | |

(Continued)

FOREIGN PATENT DOCUMENTS

| BR | 102013031854 A2 | 9/2015 |
| EP | 1604703 B1 | 8/2011 |

(Continued)

OTHER PUBLICATIONS

International Search Report and Written Opinion for PCT Application No. PCT/BR2019/050379 dated Nov. 11, 2019, 11 pages.

Primary Examiner — Nicholas J. Weiss
Assistant Examiner — Brandon W. Levy
(74) Attorney, Agent, or Firm — Dinsmore & Shohl LLP

(57) ABSTRACT

The valve has: a body projecting an inlet duct and an outlet duct; a seat in the inlet duct and cooperating with a sealing ball; a helical spring between the sealing ball and a supporting ball; a rotor mounted on the body and having a cam surface, cooperating with the supporting ball; a locking member having a magnet and housed within each cavity of the rotor, and to be moved between operative and inoperative positions; a spring in each cavity and forcing the locking member into the operative position; and retention housings, each of two of the latter being opposite to each other, receiving one of the locking members in the operative position, in a rotational position of the rotor.

20 Claims, 3 Drawing Sheets

(58) Field of Classification Search
CPC .......... A61M 2210/0693; A61M 39/22; A61M
5/14276; A61M 2202/0464; A61M
27/002; A61M 2039/248; A61M
2205/3507; A61M 2205/50; A61M
25/0127; A61M 2205/3515; A61M
2039/2493; A61M 2205/0272; A61M
2039/242; A61M 2039/2433; F16K 31/08;
F16K 35/16; F16K 15/042; F16K 17/04;
F16K 17/0406; F16K 17/286; F16K
31/52425; F16K 15/044; F16K 31/088;
F16K 27/0209; F16K 15/033; F16K
17/0486; F16K 17/22; F16K 31/0682;
F16K 31/086; Y10T 137/7256; Y10T
137/7927; Y10T 137/7905; Y10T
137/7873; F04B 53/10
See application file for complete search history.

(56) References Cited

U.S. PATENT DOCUMENTS

| | | | | |
|---|---|---|---|---|
| 9,149,615 | B2* | 10/2015 | Wilson | F16K 35/16 |
| 2005/0279960 | A1* | 12/2005 | Cabaud | A61M 27/006 |
| | | | | 251/304 |
| 2012/0302937 | A1* | 11/2012 | Barr | A61M 27/006 |
| | | | | 604/9 |
| 2013/0345646 | A1* | 12/2013 | Bertrand | F16K 31/088 |
| | | | | 604/248 |
| 2016/0220794 | A1* | 8/2016 | Negre | A61M 27/006 |

FOREIGN PATENT DOCUMENTS

| | | |
|---|---|---|
| FR | 2721520 A1 | 12/1995 |
| FR | 2816513 A1 | 5/2002 |

* cited by examiner

PROGRAMMABLE VALVE FOR THE TREATMENT OF HYDROCEPHALUS

This application is the National Stage entry of International Patent Application No. PCT/BR2019/050379 filed Sep. 6, 2019, which claims priority to Brazilian Patent Application No. BR1020180680250 filed Sep. 6, 2018, which are hereby incorporated by reference in their entirety.

TECHNICAL FIELD

The present disclosure refers to a programmable and surgically-implantable valve, to be used in a bypass system of the cerebrospinal fluid (liquor) in the treatment of hydrocephalus, to maintain the cranial intraventricular pressure at a substantially constant value in situations of disturbance in the reabsorption of liquor by the patient's own organism.

BACKGROUND

Several types of programmable valves for the treatment of hydrocephalus are known and constructed to allow the regulation of the opening pressure of the valve from the outside of the cranial cavity, in a non-invasive way and depending on the physiological condition of the patient, as it occurs with the valve described in the patent document U.S. Pat. No. 4,443,214, which valve comprises a cylindrical body of reduced height and provided with an inlet duct and with an outlet duct, opposed to each other, with the inner end of the inlet duct being provided with a conical seat against which it is seated a ball-shaped seal which is adjustably pressed against the seat by a spring blade that extends along part of the inner wall of the cylindrical body of the valve.

In this previous construction, one end of the curved spring blade is fixed to one end of a rotor in the form of a magnetic bar, which is diametrically positioned inside the cylindrical body of the valve and which can be rotated by actuation of a magnetic device, which is externally positioned to the skull of the patient, for an adjustment position adequate to the pressure of the spring blade against the ball. The ends of the rotor-bar are provided with indexing means cooperating with the internal wall of the cylindrical body, to stabilize the rotor-bar in different positions for regulating the opening of the valve seat, that is, in different positions for regulating the pressure of the spring blade on the ball of the valve.

This stabilization system presents the disadvantage in that it does not ensure the safe stabilization of the regulation when the valve is subjected to strong magnetic fields as it occurs, for example, in exams that use magnetic resonance.

Another known construction, similar to the one mentioned above, is described in U.S. Pat. No. 6,840,917, according to which the diametrical rotor-bar is replaced by an arcuate support blade, with one of the ends fixing a spring blade and carrying, in opposite positions, two magnets of the same polarity, to allow the rotational displacement, by external magnetization, of the arcuate support blade and the spring blade, to different positions for regulating the pressing of the sealing ball by the spring blade.

Despite presenting a rotor, defined by the arcuate support blade that maintains, with the internal cylindrical wall of the valve body, a better distribution of contact points, providing a safer locking of said rotor in the different regulating positions, this second solution further presents the rotational locking, for the regulating positions, depending on the degree of interference between the indexing means provided in the arcuate support blade and in the inner wall of the valve body.

The two constructions mentioned above further present the inconvenience of using a spring blade having only one of the ends fixed to the rotor, in which the mechanism for adjusting the pressure of the ball, through a region, in cantilever, of the spring blade, is subject to a greater number of mechanical variables that require greater manufacturing control to obtain precision and uniformity in the thickness of the spring blade, precision in the shape of the spring blade and uniformity in the fixation of the spring blade in the rotor. The valves that use the spring blade solution are subject to a greater standard deviation in the proposed pressures, when comparing different manufacturing batches.

Yet another known construction is described in patent document FR 2 721 520. In this third construction, the rotor is defined by a diametrical bar with an approximate "H" shape, with its center pivoted on the valve body and carrying, at each end, a locking member, which is capable of sliding, in the radial direction, between rotational locking and unlocking positions of the rotor relative to the cylindrical body of the valve. An end of the rotor-bar secures an end of a spring blade to operate against a sealing ball, as described for the two previous solutions.

Each locking member incorporates a small magnet and further an end locking portion, to be seated in one of the cavities of a circular crown, externally or internally toothed, incorporated under a cover of the valve body or internally defined within the latter, for locking the rotor in a desired rotational position of adjustment of the pressure of the spring blade against the sealing ball.

In this previous construction, the rotational locking of the rotor in the body of the valve is maintained by the use of the magnetic force of the magnets, by forcing the respective locking members to radially slide, in the respective ends of the rotor-bar, so that each respective locking portion is inserted into a cavity of the toothed circular crown.

Despite providing a safer locking compared to those obtained with the first and second constructions mentioned above, this third known construction presents, in addition to the disadvantages already mentioned and related to the use of a spring blade to press the sealing ball of the valve, the inconvenience of requiring low power magnets, because if the power of the magnets is strong, the system becomes difficult to unlock, thus making it difficult or even impossible to adjust the valve. Thus, the magnets in this solution are of low power, which also makes it difficult the rotation of the rotor, due to the lack of magnetic force.

SUMMARY

Due to the limitations and inconveniences of the well-known solutions, the present disclosure has the objective of providing a programmable and surgically implantable valve, to be used in a by-pass system of the cerebrospinal fluid (liquor) in the treatment of hydrocephalus and capable to allow a more precise control of the opening pressure of the valve with a substantial reduction of the standard deviation from the nominal pressure in each adjustment position of the valve.

An additional aim of the present disclosure is to provide a valve as mentioned above and that has its locking, in the different adjustment positions, obtained and maintained without the use of magnetic forces and also that has its unlocking, for regulating the pressure of opening, inoperative when subjected to magnetic fields, usually unilateral, and present in the external environment.

According to the present disclosure, the valve comprises conventional elements already known, such as body, cover, inlet and outlet ducts and a seat that cooperates with a sealing ball to be pressed in an adjustable manner against the seat, in order to adjust the cranial intraventricular pressure. However, in the proposed construction, the sealing ball does not come into direct contact with the internal elements for regulating the pressure against the seat, being provided an helical spring arranged inside the inlet duct, between the sealing ball and a supporting ball which protrudes partially into the body, to cooperate with a cam surface of a rotor which is mounted inside the body and which is provided with two cavities, in each one a locking member, carrying a magnet, is slidingly housed, to be linearly displaced between an operative position and an inoperative position.

The locking member is constantly forced by a spring into the operative position, rotationally locking the rotor in the valve body. Under the valve cover it is provided a circular alignment of retention housings, each of two opposing retention housings receiving one of the locking members in the operative position, at a determined rotational position of the rotor and its cam surface in relation to the supporting ball.

With the proposed constructive arrangement, the cam surface of the rotor directly acts against the supporting ball, allowing a more precise control of the opening pressure of the valve in each adjustment position of the valve, in which the rotor is safe and rotationally locked without the use of magnetic forces.

BRIEF DESCRIPTION OF THE DRAWINGS

The present disclosure will be described below, making reference to the accompanying drawings, given by way of example only and in which.

DETAILED DESCRIPTION

Figure 1:
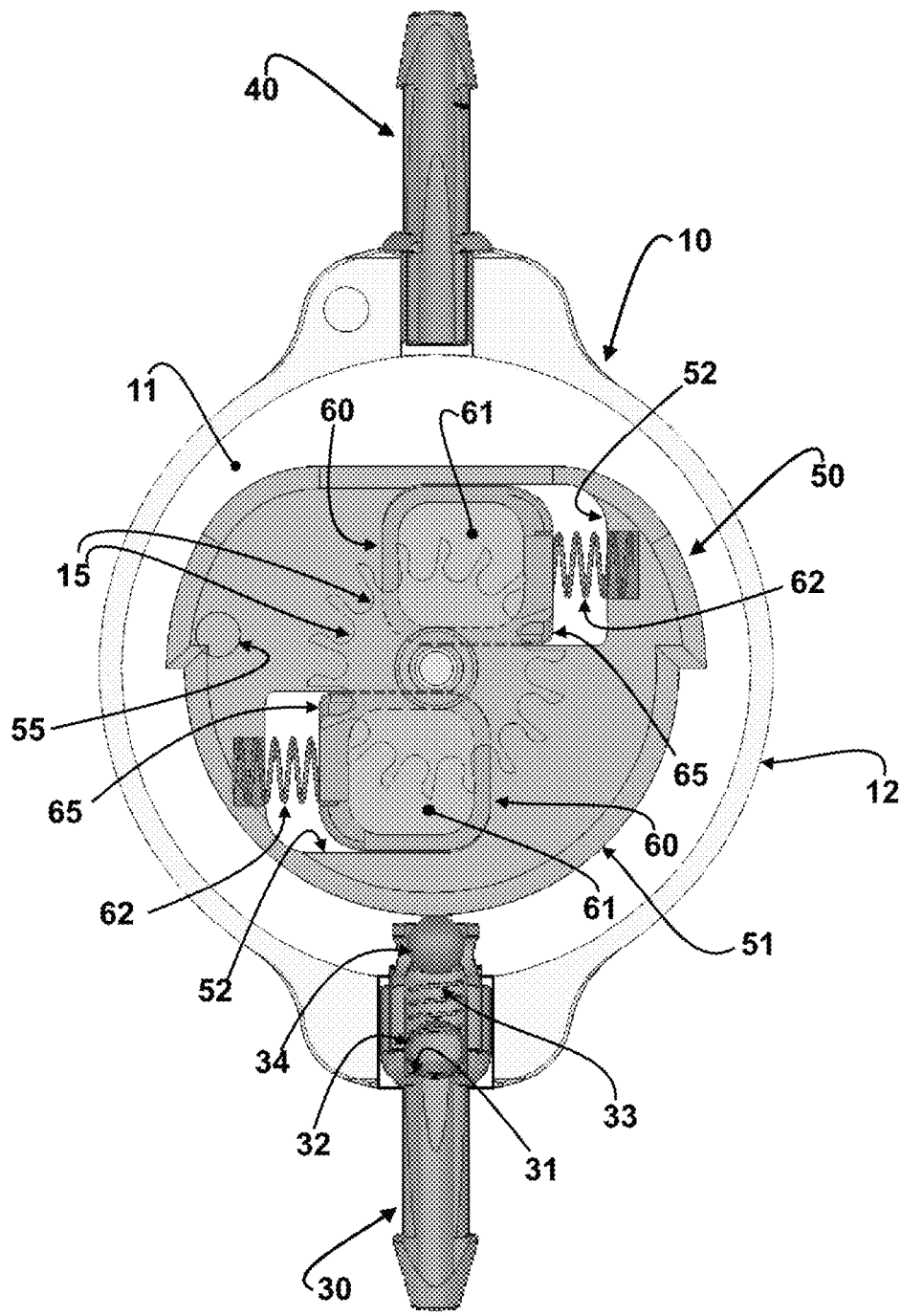
FIG. 1 represents a plan view of the valve of the present disclosure, when devoid of its cover and having the inlet and outlet ducts diametrical and longitudinally cut.
Figure 2:
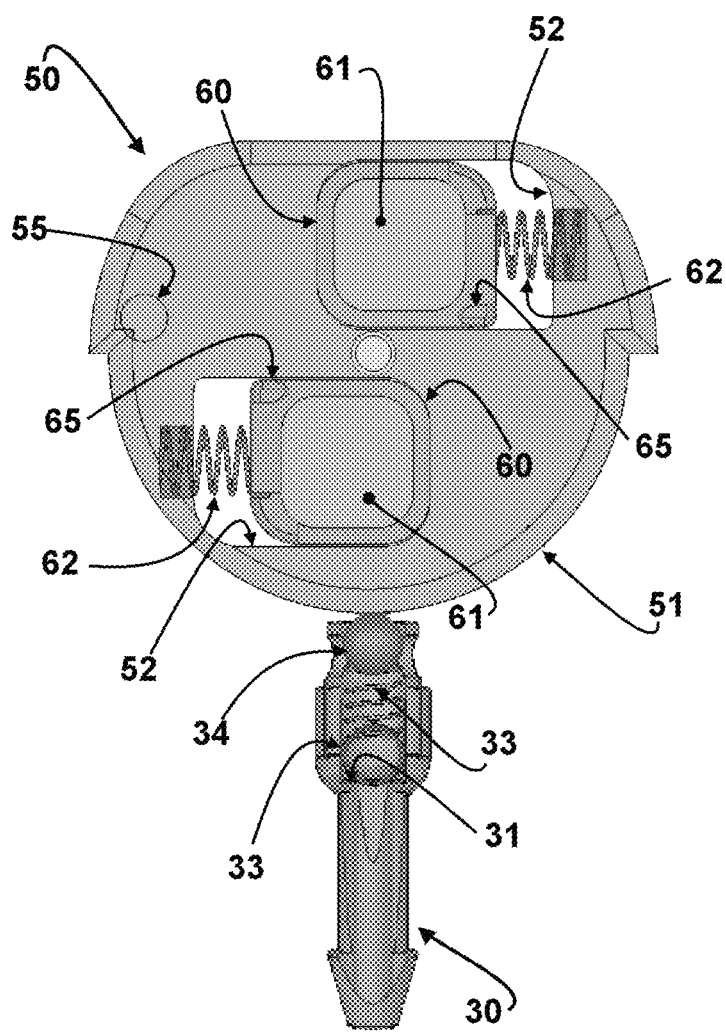
FIG. 2 represents a plan view of the rotor and the inlet duct, housing the valve seat and the sealing elements.
Figure 3:
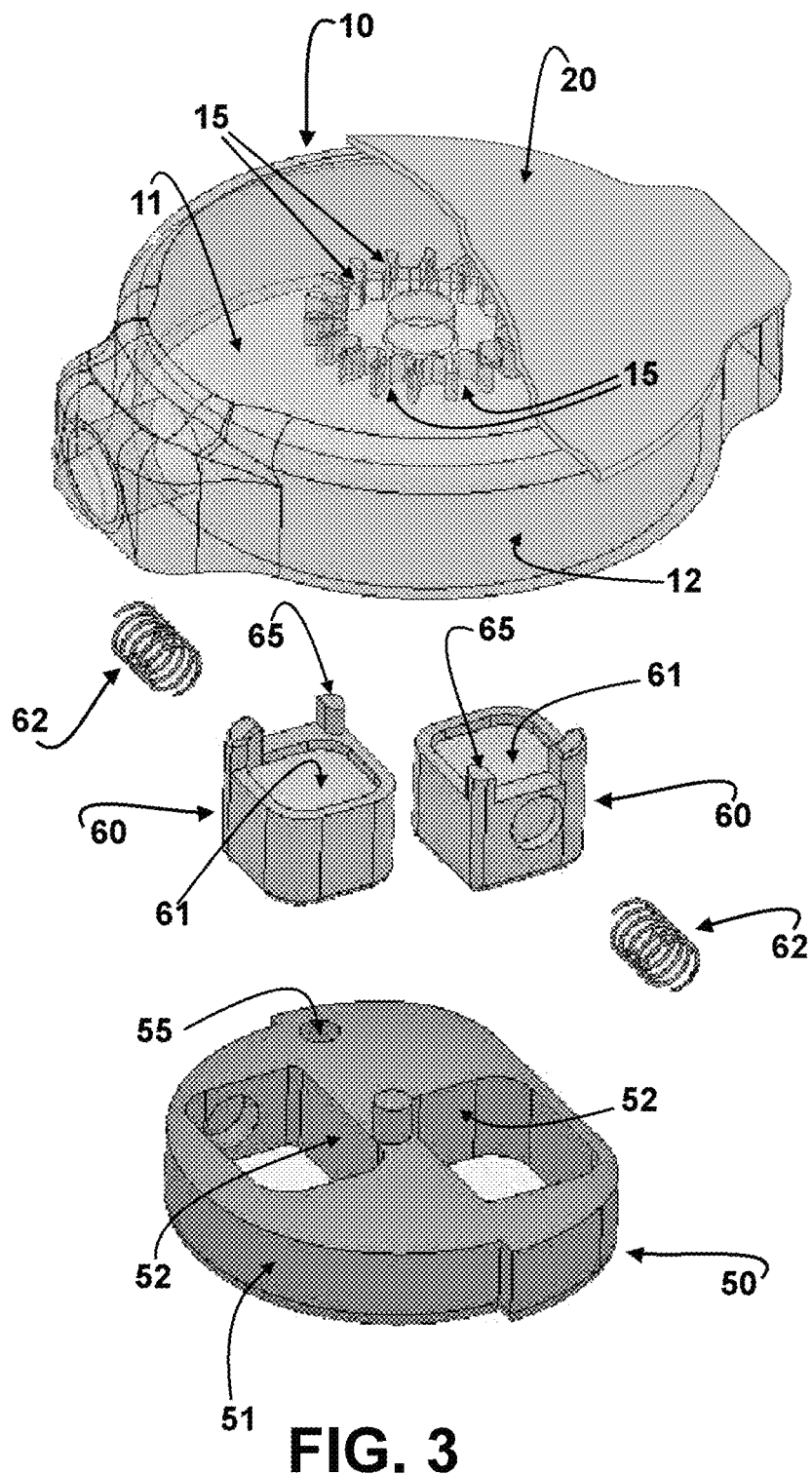
FIG. 3 represents an exploded perspective view of the valve, illustrating part of the cover, the rotor and the rotational locking members of the rotor in the valve body.

As previously mentioned and illustrated in the accompanying drawings, the present disclosure relates to a programmable valve for treating hydrocephalus and which comprises: a body 10 of reduced height and formed by a bottom wall 11 and a cylindrical side wall 12 that it is superiorly closed by a cover 20, these elements being constructed in a known manner in the state of the art and using suitable biocompatible materials.

An inlet duct 30 is also conventionally provided with an inner end open to the interior of the body 10 through the side wall 12 of the latter and an outer end to be inserted into the cerebral ventricle of the patient, and an outlet duct 40, generally opposite to the inlet duct 30 and having an inner end open to the interior of the body 10 through the side wall 12 of the latter and an outer end to be inserted into the peritoneum of the patient.

According to the present disclosure, the inner end of the inlet duct 30 houses a seat 31, generally conical, cooperating with a sealing ball 32 against which it is seated an end of an helical spring 33 in which opposite end is seated a supporting ball 34 which protrudes radial and partially into the interior of the body 10.

A rotor 50, generally of circular contour, is mounted, by a rotation shaft 55, inside the body 10 and has a cam surface 51 defined by an extension of the peripheral edge of the rotor 50. In the constructive form illustrated, the cam surface 51 takes the shape of a circle arc, whereby the axis of the rotation shaft 55 of the rotor 50 is eccentrically arranged in relation to the cam surface 51. However, it is possible to maintain the rotation shaft 55 of the rotor 50 in a central position and to configure the cam surface 51 into a progressively eccentric shape.

With the rotational displacement of the rotor 50, its cam surface 51 cooperates with the supporting ball 34, pressing it, with more or less intensity, causing a corresponding greater or lesser compression of the helical spring 33 and the sealing ball 32 against the seat 31, adjusting the pressure to the resistance to the passage of the liquor.

The rotor 50 is further provided with two cavities 52 which are rectangular, parallel to each other and positioned in opposite hemispheres and sides of the rotor 50. The longitudinal axes of the cavities 52 are orthogonal to the longitudinal axis of the valve, wherein in each cavity 52 is slidingly housed a locking member 60, carrying a magnet 61 of defined polarity. The cavities 52 are dimensioned to allow the locking members 60 to be linearly displaced, in mutually opposite directions, between an operative position, in which the rotor 50 is rotationally locked in relation to the body 10, and an inoperative position, which allows the rotor 50 to be rotated around its rotation shaft 55, for different adjustment positions of the valve.

Each locking member 60 is constantly forced into the operative position, illustrated in the drawings, by a respective spring 62 mounted in each cavity 52. The locking members 60 are forced, by the respective springs 62, towards the central axis of the body 10 to the operative locking position.

For providing rotational locking of the rotor 50, the valve further comprises a circular alignment of retention housings 15 which, in the illustrated configuration, are provided under the cover 20, wherein each of two opposite retention housings 15 receives one of the locking members 60 in the operative position, in a determined rotational position of the rotor 50 and its cam surface 51 in relation to the supporting ball 34.

It should be understood that the circular alignment of retention housings 15 can be provided on the bottom wall 11 of the body 10, in an inverted position in relation to that illustrated in the drawings, without changing the functional concept of the valve.

More specifically, each locking member 60 carries, in a portion of the edge facing the center of the rotor 50, a pin 65 which, in the illustrated configuration, projects upwardly, to be received in a respective retention housing 15. When the locking member 60 is displaced to its operative position, by actuation of the spring 62. If the circular alignment of retention housings 15 is provided on the bottom wall 11 of the body 10, the pin 65, of each locking member 60, will project downwardly.

For the rotational unlocking of the rotor 50 in relation to the body 10, it is used an adjustment device (not shown), which is constructed so that, when it is approached to the cranial cavity of the patient causes, by magnetic actuation, the displacement of the locking members 60 to the inoperative position, releasing the locking members 60 in relation to the retention housings 15, rotationally unlocking the rotor 50 in relation to the body 10. This is due to the fact that the magnets 61 are subjected to respective external magnetic fields of the adjustment device, presenting the intensity and polarity to overcome the force of the springs 62.

With the rotational unlocking of the rotor 50, the latter can be rotated to a new adjustment position in the pressing of the sealing ball 32 against the seat 31, also by action of magnetic traction force on the same magnets 61.

After the valve adjustment operation is finished, the adjustment device is moved away from the valve, allowing the springs 62 to move the locking members 60 back to the operative locking position.

The magnets 61 have the same polarity, so that the magnetic fields present in the environment or unilateral ones are able to move only one of the locking members 60, while the other locking member is forced to remain with its magnet 61 in the operative locking position, avoiding the involuntary unlocking of the rotor 50.

Although only one embodiment of the valve has been presented herein, it should be understood that changes in the shape and arrangement of different component parts of the valve may be made, without deviating from the inventive concept defined in the claim set which accompanies the present description.

The invention claimed is:

1. A programmable valve for the treatment of hydrocephalus and adjustable from the outside, the valve comprising:
   a body having a bottom wall and a cylindrical side wall closed by a cover and through which an inlet duct, configured to be inserted into a cerebral ventricle of a patient, and an outlet duct, configured to be inserted into a peritoneum of the patient, are open to an interior of the body;
   a seat housed in the inlet duct, the seat cooperating with a sealing ball and a helical spring disposed between the sealing ball and a supporting ball that partially protrudes to the interior of the body;
   a rotor mounted, by a rotation shaft, inside the body and having a cam surface, cooperating with the supporting ball, and two cavities, rectangular and parallel to each other and positioned on opposite hemispheres and sides of the rotor;
   a locking member carrying a magnet and slidingly housed inside each cavity, to be linearly displaced, in a direction opposite to that of the other locking member, between an operative position and an inoperative position;
   a spring mounted in each cavity and forcing each locking member into the operative position; and
   a circular alignment of retention housings provided inside the body, each of two retention housings being opposite, and receiving one of the locking members in the operative position, in a rotational position the rotor and of the cam surface in relation to the supporting ball,
   wherein the rotation shaft is noncoaxially aligned with a center of the retention housings.

2. The valve according to claim 1, wherein the cam surface of the rotor is defined by an extension of a peripheral edge of the rotor.

3. The valve according to claim 2, wherein the cam surface is in a shape of a circle arc and wherein the rotation shaft of the rotor is eccentrically arranged with respect to the cam surface.

4. The valve according to claim 3, wherein each spring forces each locking member towards the central axis of the body, to the operative locking position.

5. The valve according to claim 4, wherein the magnets are arranged such that an outer face of each of the magnets have the same polarity.

6. The valve according to claim 3, wherein the magnets are arranged such that an outer face of each of the magnets have the same polarity.

7. The valve according to claim 3, wherein each locking member carries, in a portion of an edge facing a center of the rotor, a pin, projecting from the locking member and to be received in a respective retention housing when the locking member is displaced to the operative position.

8. The valve according to claim 2, wherein each spring forces each locking member towards the central axis of the body, to the operative locking position.

9. The valve according to claim 8, wherein the magnets are arranged such that an outer face of each of the magnets have the same polarity.

10. The valve according to claim 8, wherein each locking member carries, in a portion of an edge facing a center of the rotor, a pin, projecting from the locking member and to be received in a respective retention housing when the locking member is displaced to the operative position.

11. The valve according to claim 2, wherein the magnets are arranged such that an outer face of each of the magnets have the same polarity.

12. The valve according to claim 2, wherein each locking member carries, in a portion of an edge facing a center of the rotor, a pin, projecting from the locking member and to be received in a respective retention housing when the locking member is displaced to the operative position.

13. The valve according to claim 1, wherein each spring forces each locking member towards a central axis of the body, to the operative locking position.

14. The valve according to claim 13, wherein the magnets are arranged such that an outer face of each of the magnets have the same polarity.

15. The valve according to claim 13, wherein each locking member carries, in a portion of an edge facing a center of the rotor, a pin, projecting from the locking member and to be received in a respective retention housing when the locking member is displaced to the operative position.

16. The valve according to claim 1, wherein the magnets are arranged such that an outer face of each of the magnets have the same polarity.

17. The valve according to claim 16, wherein each locking member carries, in a portion of an edge facing a center of the rotor, a pin, projecting from the locking member and to be received in a respective retention housing when the locking member is displaced to the operative position.

18. The valve according to claim 1, wherein each locking member carries, in a portion of an edge facing a center of the rotor, a pin, projecting from the locking member and to be received in a respective retention housing when the locking member is displaced to the operative position.

19. The valve according to claim 18, wherein the circular alignment of retention housings is provided under the cover and the pin is projected upwardly.

20. The valve according to claim 1, wherein the locking members are moved to the inoperative position, releasing the locking members in relation to the retention housings, rotationally unlocking the rotor in relation to the body, when the magnets are submitted to respective external magnetic fields with intensity and polarity necessary to overcome a force of the springs.

* * * * *